(12) United States Patent
Higgins

(10) Patent No.: US 8,121,812 B2
(45) Date of Patent: Feb. 21, 2012

(54) AC MAGNETIC TRACKING WITH PHASE DISAMBIGUATION

(75) Inventor: Robert F. Higgins, South Burlington, VT (US)

(73) Assignee: ALKEN Inc., Colchester, VT (US)

( * ) Notice: Subject to any disclaimer, the term of this patent is extended or adjusted under 35 U.S.C. 154(b) by 704 days.

(21) Appl. No.: 12/283,296

(22) Filed: Sep. 10, 2008

(65) Prior Publication Data

US 2009/0076746 A1    Mar. 19, 2009

Related U.S. Application Data

(60) Provisional application No. 60/993,875, filed on Sep. 14, 2007.

(51) Int. Cl.
*G01C 17/00* (2006.01)
*H01F 5/00* (2006.01)

(52) U.S. Cl. .................... 702/153; 702/152; 324/207.17

(58) Field of Classification Search .................. 702/153
See application file for complete search history.

(56) References Cited

U.S. PATENT DOCUMENTS

| | | | | |
|---|---|---|---|---|
| 4,328,548 A * | 5/1982 | Crow et al. | .................... | 701/207 |
| 6,838,873 B2 * | 1/2005 | James et al. | ............. | 324/207.22 |
| 7,015,859 B2 | 3/2006 | Anderson | | |
| 7,096,148 B2 | 8/2006 | Anderson et al. | | |
| 7,251,366 B1 * | 7/2007 | Silver et al. | .................... | 382/209 |
| 7,451,549 B1 * | 11/2008 | Sodhi et al. | ...................... | 33/356 |
| 2005/0246122 A1 * | 11/2005 | Jones et al. | .................... | 702/107 |
| 2007/0013657 A1 * | 1/2007 | Banning | ........................ | 345/157 |
| 2007/0055125 A1 * | 3/2007 | Anderson et al. | ............. | 600/407 |
| 2009/0030646 A1 * | 1/2009 | Jones et al. | .................... | 702/150 |

OTHER PUBLICATIONS

International Search Report issued in connection with corresponding International Appln. No. PCT/US08/10631, 2008.

* cited by examiner

*Primary Examiner* — Jonathan Teixeira Moffat
(74) *Attorney, Agent, or Firm* — Lerner, David, Littenberg, Krumholz & Mentlik, LLP

(57) ABSTRACT

A method and system for magnetic locating resolves phase ambiguity. The system uses time-division multiplexed magnetic fields emitted from plural transmit coils. The magnetic fields are alternating fields at a carrier frequency, and the fields emitted from different coils in different transmit intervals have known phase relationship with one another as, for example where the alternating fields are coherent with one another. A receiver uses a plurality of sensor coils and derives plural components using the common phase reference or plural phase reference times having a known relationship. If the determinant of a matrix of the components has a first value, the phase information in the components is correct, and position and orientation are derived from the components. If the determinant has a second value, the phase information in the components is incorrect. In this case, corrected components are formed by shifting the phases of the components $\pi$ radians; the position and orientation are derived from the corrected components.

27 Claims, 4 Drawing Sheets

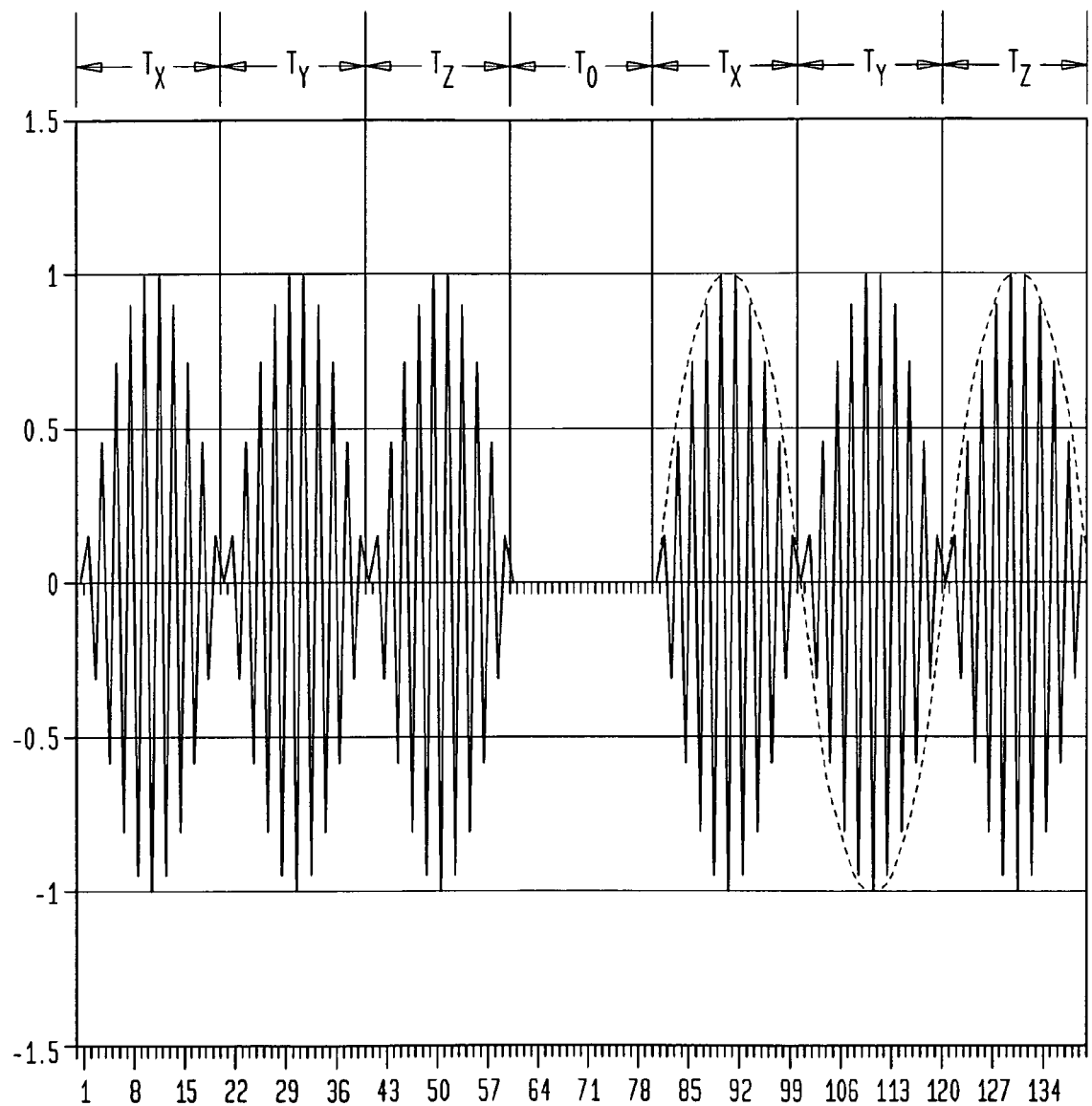

AC MAGNETIC TRACKING WITH PHASE DISAMBIGUATION

CROSS-REFERENCE TO RELATED APPLICATIONS

The present application claims benefit of the filing date of U.S. Provisional Patent Application No. 60/993,875, filed Sep. 14, 2007, the disclosure of which is incorporated by reference herein.

FIELD OF THE INVENTION

The present invention relates to magnetic locators, commonly also referred to as magnetic tracking systems.

BACKGROUND OF THE INVENTION

A magnetic tracking system includes a sender or transmitter which applies magnetic fields in space, and a sensor which detects the fields. Most commonly, the transmitter includes three coils directed along three mutually orthogonal axes. Typically, these coils are co-located, i.e., wound so that their centers are at or very near to the same point in space. The sensor or receiver typically includes a similar assembly of three coils or other sensors. The position and orientation of the receiver in the frame of reference of the transmitter can be determined from the set of relationships between each transmitter coil and each coil or sensor of the receiver. Thus, each transmitter coil is actuated to emit a magnetic field and the resulting magnetic field component in the direction of each sensor coil or other sensor is measured by the receiver.

Magnetic locating systems of this type are used in many applications. For example, the receiver may be attached to a surgical instrument so that the instrument can be tracked in the frame of reference of the operating room, or in the frame of reference of a previously acquired image of the patient. Also, a probe having a receiver mounted thereon can cooperate with a fixed transmitter so that as the probe is moved over the surface of a three-dimensional object, the contours of the object are deduced from the position of the probe. In still other applications, the sensor may be mounted on a part of a human body and used to measure the position and orientation of that body part relative to a frame of reference holding the transmitter. For example, a head-mounted sensor can be used to detect the direction in which a user has turned his or her head. In still other arrangements, a magnetic locating system may serve as a three-dimensional input tool for a computer or computer game. Although the various applications have been described with reference to a moving receiver and a fixed transmitter or sender, these can be reversed, so that the transmitter moves in the frame of reference of the sensor.

In a frequency-multiplexed AC system, each of the transmitter coils is driven at a different frequency, most commonly with a continuous sinusoidal signal at such frequency. If the sensor is in an arbitrary orientation relative to the transmitter, the axes of the sensor coils will not be aligned with the axes of the transmitter coils. In this case, each sensor coil detects the magnetic fields generated by all of the transmitter coils, so that each sensor coil delivers a composite coil signal which includes components at each of the transmitted frequencies. The components in each sensor signal are separated from one another by techniques such as filtering or, most commonly, Fourier transformation of the sensor signal to yield a frequency domain representation. The separated components provide nine separate components, each of which represents the signal induced in one sensor coil by one transmitter coil. For example, there is a component $S_{XY}$ representing the signal induced on the sensor coil oriented in the X-direction of the receiver by the field from the coil oriented in the Y-direction of the transmitter. Similarly, there is a signal $S_{XX}$ representing the signal induced in the sensor coil oriented in the X-direction of the receiver by the field emitted from the coil oriented in the X-direction of the transmitter.

The position and orientation of the sensor in the frame of reference of the transmitter can be computed from the phase and amplitude of the various components. Algorithms for accomplishing this are shown, for example, in Jones, U.S. Pat. No. 4,737,794; Egli et al., U.S. Pat. No. 4,287,809; and Raab, U.S. Pat. No. 4,314,251, the disclosures of which are hereby incorporated by reference herein.

However, the phase of the received signal components relative to the phase of the transmitted field components must be known. In a "wired" system, the receiver is connected to the transmitter, so that the receiver operates in synchronism with the transmitter. Therefore, the receiver can directly determine the phase of the sensor signal components using the same timing reference employed by the sender.

In some applications, however, a wire or other direct connection between the sender and the sensor is undesirable or impractical. Therefore, wireless systems have been developed. Examples of wireless systems are disclosed in U.S. Published Patent Application No. 2005/0285590 ("the '590 Publication") and in Anderson, U.S. Pat. No. 7,015,859 ("the '859 patent"). In a wireless system, the receiver is not synchronized with the transmitter unit. In general, the receiver cannot detect the phase of the signals used to drive the transmitter coils without ambiguity. For example, as the sensor moves past the center point of the transmitter in one of the three directions constituting the frame of reference of the transmitter, the sign of a signal component reverses. This reverses the phase of the signal component in exactly the same manner as if the phase of the signal used to drive a transmitter coil was shifted 180° or π radians.

Accordingly, further improvement would be desirable.

SUMMARY OF THE INVENTION

One aspect of the invention provides methods of magnetic locating. A method according to this aspect of the invention desirably includes the step of actuating a plurality of co-located orthogonal transmit coils in alternating sequence to emit a time-multiplexed sequence of magnetic fields $M_B$ during successive transmit intervals, where the subscript B denotes one of the transmit coils, each magnetic field varying at a carrier frequency f. The magnetic fields have a known phase relationship with one another. For example, the magnetic fields may be coherent with one another.

The method desirably includes sensing the alternating magnetic fields using a plurality of orthogonal sensor coils at a receiver so that each sensor coil generates a sensor signal during each transmit interval of the time-multiplexed sequence used by the transmitter. The method most preferably also includes the step of deriving a set of components $C_{AB}$ at frequency f from the sensor signals, wherein the subscript A denotes the particular receiving coil which received such component and the subscript B denotes the transmitter coil active during the transmit interval. Each component $C_{AB}$ has amplitude and phase. The phases of the components are determined with respect to phase reference times. The phase reference times used in successive transmit intervals are offset from one another by known amounts. For example, where the components are derived by sampling the sensor signals during an active sampling period in each transmit interval and performing a Fourier transform on the resulting sets of samples, the phase derived from the Fourier transform may be implicitly referenced to the beginning times of the active sampling periods. Desirably, the beginning times of the active sampling periods used for successive transmit intervals are offset from one another by dwell times, each such dwell time being equal to an integral number of periods of the carrier frequency. As further discussed below, the method yields phase information in all of the components with only two possibilities: either all of the phase information is accurate; or all of the phase information is inaccurate by $\pi$ radians.

The method most preferably includes the steps of forming a matrix of the components $C_{AB}$ with each row having the same value of A and each column having the same value of B, and computing the determinant of the matrix. If the determinant is positive, the phase information is accurate. In this case, the position and orientation of the sensor coils relative to the transmit coils is calculated based upon the signal components $C_{AB}$. If the determinant is negative, the phase information is incorrect by $\pi$. In this case, the method branches to the further step of deriving inverted signal components $C'_{AB}$ corresponding to the signal components $C_{AB}$ phase-shifted by $\pi$ radians, and calculating the position and orientation of the sensor coils relative to the transmit coils based upon the inverted signal components.

As further explained below, the method resolves the phase ambiguity inherently present in the sensor signals and in the components derived from the sensor signals, without the complex measures commonly used to resolve phase ambiguity in frequency-multiplexed magnetic locating systems.

A further aspect of the invention provides magnetic locating systems. The magnetic locating system in accordance with this aspect of the invention includes a transmitter having a plurality of co-located orthogonal transmit coils and a transmitter circuit arranged to actuate the coils in the manner discussed above. For example, the transmitter circuit may include a drive circuit associated with each of the transmit coils, a carrier frequency generator for generating a carrier frequency signal and a multiplexer for applying the carrier frequency signal to the various drive circuits in succession. By using the same carrier frequency signal to actuate all of the drive circuits and hence all of the coils, the system assures coherence between the alternating magnetic fields emitted by the various coils.

The system desirably also includes a receiver having a plurality of co-located orthogonal sensor coils, and a receiver circuit arranged to perform the functions discussed above.

BRIEF DESCRIPTION OF THE DRAWINGS

FIG. 4 is a diagrammatic representation of a signal used in a system according to a further embodiment of the invention.

DETAILED DESCRIPTION

Figure 1:
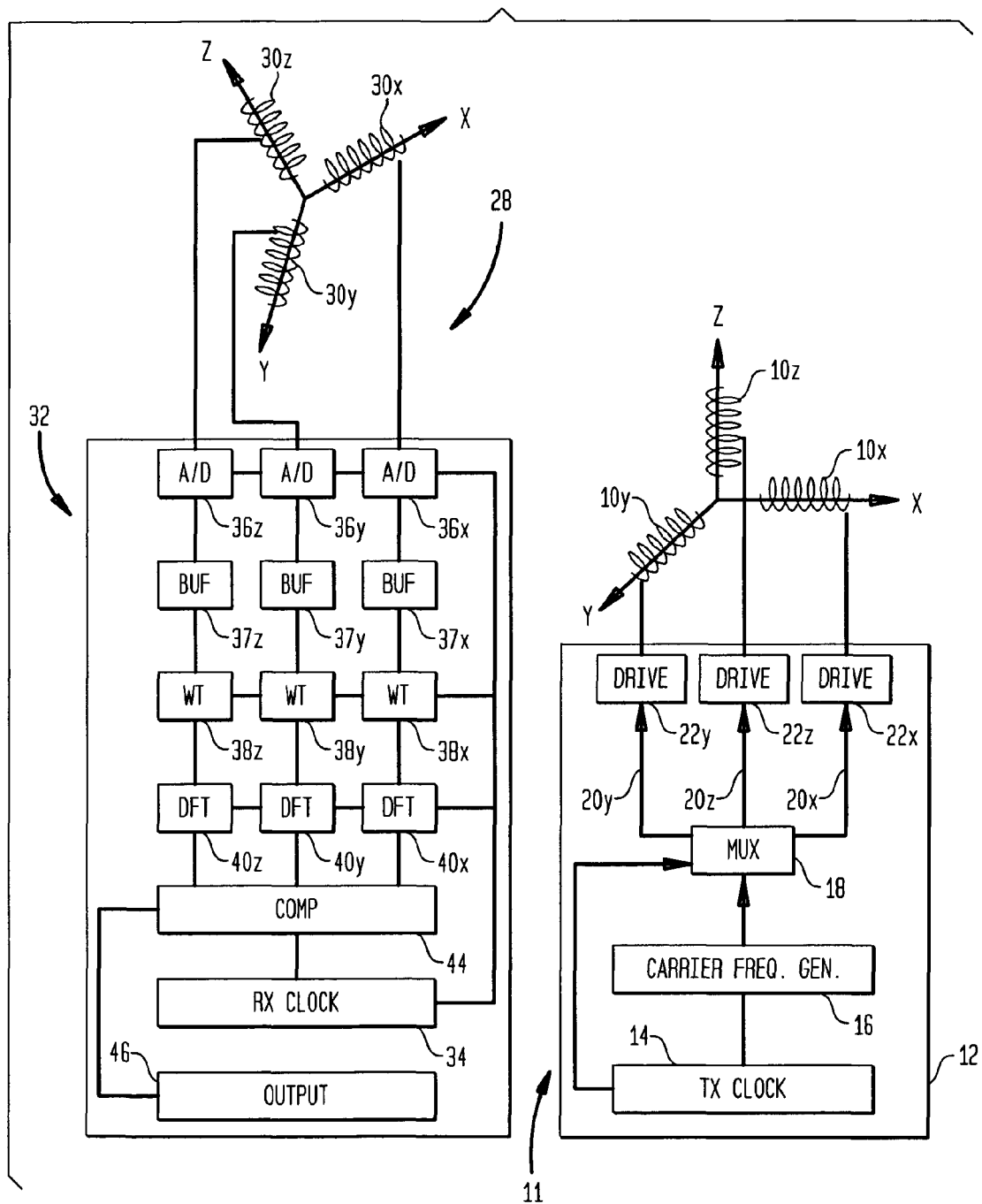
FIG. 1 is a functional block diagram of apparatus in accordance with one embodiment of the invention.

In the description below and the accompanying drawings, functional elements of the receiver are shown and described as separate circuits for ease of understanding. Likewise, functional elements of the transmitter are shown and described as separate circuits. However, this should not be taken as requiring separate physical components. For example, a programmable component such as a microprocessor or ASIC may be arranged to fulfill the roles of different circuit elements at different times, and a single component may serve as part or all of two or more of the functionally-described separate circuits. Merely by way of example, many or all of the functions of the receiver control circuit 32 (FIG. 1) may be performed by a programmable signal processing chip.

A transmitter 11 in accordance with one embodiment of the invention includes a set of three collocated coils 10x, 10y and 10z disposed along three mutually orthogonal axes, arbitrarily labeled "X," "Y," and "Z". The axes of the coils define a conventional Cartesian coordinate system or frame of reference. Although the coils are shown as separated from one another for clarity of illustration, in practice, the coils desirably have their centers as close as practicable to a common central point. The transmitter further includes a transmitter control circuit 12, which is adapted to drive each of the coils as discussed below. In the particular embodiment depicted, the transmitter control circuit includes a digital transmitter clock 14 and a carrier frequency generator 12. Carrier frequency generator 16 may be a conventional oscillator arranged to generate a continuous sinusoidal signal at a frequency referred to herein as the "carrier" frequency. For typical applications, the carrier frequency is in the KHz range, such as at 12 KHz. The oscillator may be locked to the digital transmitter clock to assure coherence. Alternatively, the carrier frequency generator may include a microprocessor arranged to calculate the successive values which constitute a continuous sinusoidal waveform and a digital to analog (D/A) converter. In a further alternative, carrier frequency generator 16 may include a memory with the successive values constituting the desired sinusoidal waveform and operative to read out in these values in sequence when the memory is clocked by transmitter clock 14, together with a D/A converter. In any of these arrangements, the carrier frequency generator may include one or more amplifiers for amplifying the sinusoidal signal to the desired level and for isolating the signal-generating elements from other elements of the circuit.

Carrier frequency generator 16 is connected to a multiplexer 18 which is timed by transmitter clock 14. The multiplexer has three outputs 20x, 20y and 20z. As further discussed below, the multiplexer is arranged to apply the carrier frequency signal from generator 16 to the outputs in an alternating sequence including a quiet period during which the multiplexer does not connect the carrier frequency signal to any of the outputs.

Output 20x of multiplexer 18 is connected to a drive circuit 22x, which in turn is connected to coil 10x. Multiplexer output 20y is connected to a drive circuit 22y which in turn is connected to coil 10y, whereas multiplexer output 20z is connected to drive circuit 22z, which in turn is connected to coil 10z. Each drive circuit 22 includes elements such as one or more capacitors selected so that the drive circuit, together with the inductance of associated coil 10, constitutes a resonant circuit having a resonant frequency substantially equal to the carrier frequency. Each drive circuit 22 may also include additional components such as one or more power amplifiers (not shown). Each drive circuit 22 is arranged to drive the associated coil 10 with an alternating current at the carrier frequency in response to a carrier frequency signal applied by the associated multiplexer output 20. Preferably, the all of the drive circuits, together with the associated coils, provide substantially similar response characteristics. The phase delay, if any, between the carrier frequency signal applied at the multiplexer output and the alternating current in the associated coil 10 desirably is substantially the same for all of the drive circuits 22.

Figure 2:
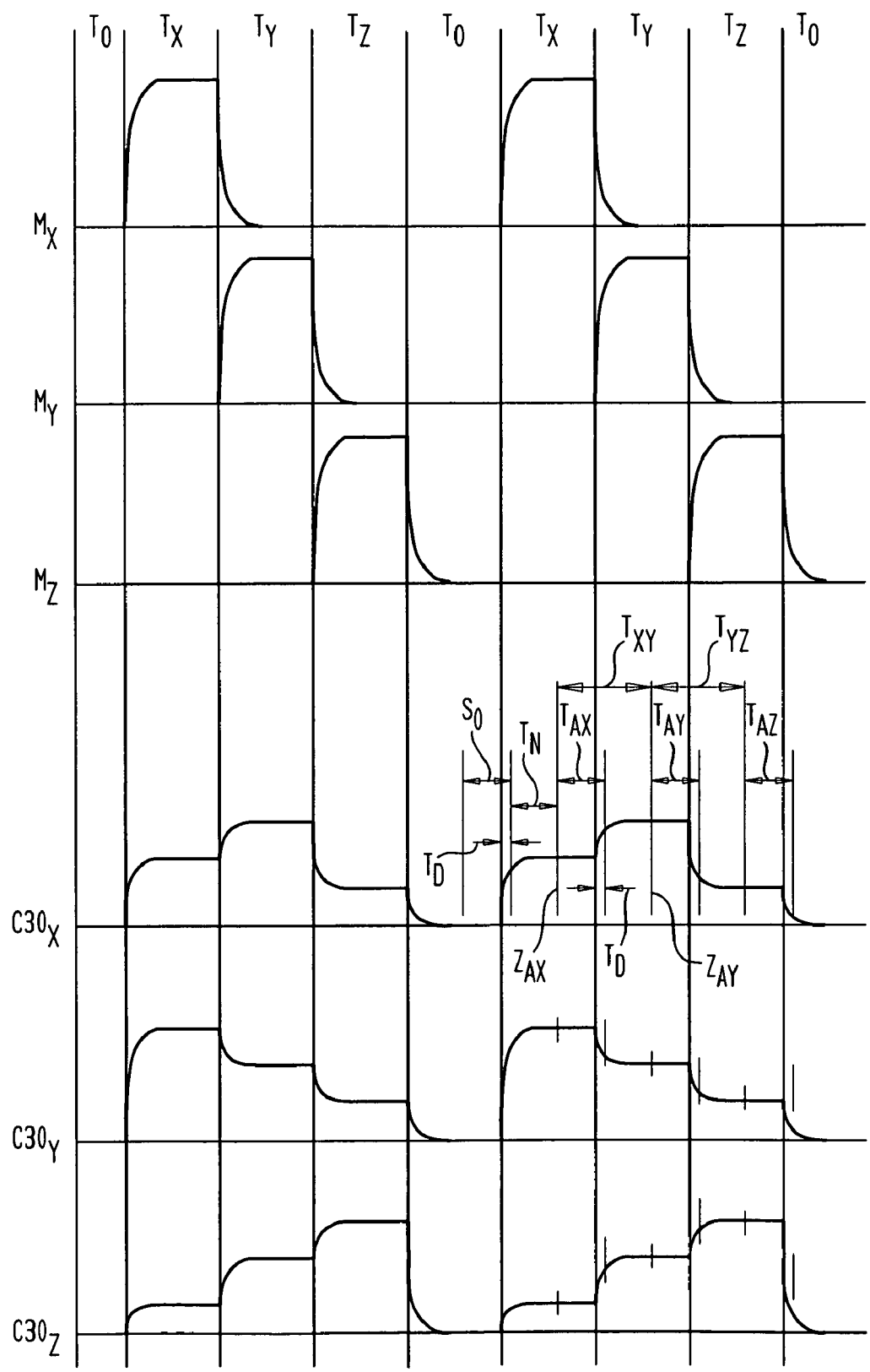
FIG. 2 is a diagrammatic representation of certain signals used in the apparatus of FIG. 1.

The transmitter actuates the coils to send magnetic fields in a repeating sequence as shown in FIG. 2. During a quiet period $T_O$, the multiplexer does not connect the carrier frequency signal from generator 16 to any of the outputs 20, and therefore all of the drive circuits 22 and transmitter coils 10 are quiescent. An X-coil transmit interval $T_X$ begins at the end of quiet period $T_O$. During interval $T_X$, the multiplexer 18 connects the carrier frequency signal only to output 20x and hence to drive circuit 22x, so that coil 10x emits an alternating magnetic field at the carrier frequency. The amplitude of this alternating field is shown by $M_X$ in FIG. 2. At the end of interval $T_X$, a Y-coil drive interval $T_Y$ begins. During interval $T_Y$, multiplexer 18 connects the carrier frequency signal to drive circuit 22y, and coil 10y emits an alternating magnetic field with amplitude $M_Y$ (FIG. 2). Interval $T_Y$ is followed by an interval $T_Z$, during which the carrier frequency is connected to drive circuit 22z and coil 10z emits magnetic field $M_Z$. At the end of $T_Z$, the sequence repeats, starting with a further quiet period $T_0$. As further explained below, the end of the quiet period $T_0$ provides a marker denoting a particular point in the sequence of intervals, which can be detected by the receiver.

The alternating magnetic fields emitted by the various coils are coherent with one another. That is, the time from a particular phase of the waveform emitted by coil 10X during interval $T_X$ to the corresponding phase of the waveform emitted by coil 10y during interval $T_Y$ is equal to an integral number of periods of the carrier frequency. Similarly, the time from a particular phase of the waveform of coil 10x during interval $T_X$ to the corresponding phase of the waveform emitted by coil 10z during interval $T_Z$ is also equal to an integral number of periods of the carrier frequency. In the particular embodiment depicted, this coherence arises from the use of a single continuously-operating carrier frequency generator 16 to drive all of the coils. Stated another way, in the particular embodiment depicted, the alternating magnetic field from each transmit coil is a replica of the waveform from carrier frequency generator 16.

In the embodiment depicted, the duration of each interval in the sequence is equal to an integral number of periods of the carrier frequency. Stated another way, the carrier frequency is an integral multiple of the rate at which the multiplexer switches between intervals. With a carrier frequency of 12 KHz, the switching rate may be 375 Hz, so that each transmit interval is approximately 2.666 milliseconds, or 32 periods of the carrier frequency.

Each of the resonant circuits formed by the coils and drive circuits has a finite stabilization time. Thus, as shown in FIG. 2, $M_X$ rises asymptotically to a stable magnitude during a short but finite time after the beginning of interval $T_X$ and falls asymptotically to 0 during a short but finite time after the end of $T_X$ and the beginning of $T_Y$. The other magnetic fields $M_Y$ and $M_Z$ have similar rise and fall times at the beginning and end of the other intervals $T_Y$ and $T_Z$. The rise time may be taken as the time required for the magnetic field from a given coil to reach about 90% of its stable value. The rise time desirably is less than half of the duration of a single transmit interval $T_X$, $T_Y$, or $T_Z$. The fall time required for each alternating magnetic field M to decay to about 10% of its stable value desirably also is less than about half the duration of a single transmit interval. As shown in FIG. 2, the fall time of $M_X$ coincides with the rise time of $M_Y$ at the beginning of $T_Y$, whereas the fall time of $M_Y$ coincides with the rise time of $M_Z$ at the beginning of $T_Z$.

The receiver 28 used with transmitter 11 includes a set of three collocated sensors in the form of coils 30x, 30y, and 30z. Like the transmitter coils, the receiver or sensor coils 30x, 30y, and 30z are oriented along three orthogonal axes denoted X, Y, or Z. However, because the receiver is free to move relative to the transmitter, the X, Y, and Z axes of the receiver lie at an unknown orientation in the frame of reference of the transmitter coils 10.

Each sensor coil generates an electrical signal representing the magnetic fields impinging on that coil. Receiver 28 includes a receiver circuit 32 connected to the coils. The receiver circuit includes a receiver clock 34 and analog-to-digital converters 36x, 36y, and 36z linked through preamplifiers (not shown) to coils 30x, 30y, and 30z, respectively. Thus, each A/D converter samples the signal appearing on an associated one of the sensor coils. The A/D converters 36 operate at a sample rate substantially higher than the carrier frequency, and most preferably at a sample rate which is an integral multiple of the carrier frequency. For example, in an embodiment where the carrier frequency is 12 KHz, the sampling rate may be 48 KHz, i.e., 4 times the carrier frequency, and the time between successive samples, referred to herein as the sampling interval, is one-fourth of the period of the carrier frequency. As mentioned above, each transmission interval desirably corresponds to 32 periods of the carrier frequency, and hence 128 sampling intervals. The A/D converters 36 operate simultaneously with one another to capture samples of the signals from the various coils at the same sampling times.

The receiver control circuit 32 includes a set of three storage buffers 37x, 37y, and 37z, each capable of storing the samples from a set of 512 sampling intervals. 512 sampling intervals encompass a full set of one complete quiet period, and complete transmit intervals $T_X$, $T_Y$, and $T_Z$. The samples are stored in the buffer in order from 1st to 512th. As further discussed below, the set of samples is treated as "circular," i.e., the 1st sample follows immediately after the 512th sample. The receiver control circuit 32 also includes windowing or weighting circuits 38x, 38y, and 38z. The windowing circuits are connected to receive the successive samples from the A/D converters 36. The windowing circuits subdivide the successive samples into small sets, each representing a very short interval or "window" and apply a weighting function to the samples within each set based on the timing of the samples within the window. In general, a weighting function multiplies the digital value of each sample by a coefficient which depends on the timing of each sample within the window. Weighting or windowing functions of this type are well known in the art of digital signal processing. In general, the object of a weighting function is to treat the samples in such a manner that the response of a discrete Fourier transform applied to the samples will be reasonably consistent over a wide range of frequencies. One example of such a weighting function is the well-known Blackman-Harris windowing function.

The receiver control circuit further includes discrete Fourier transform ("DFT") circuits 40x, 40y, and 40z. Each DFT circuit operates cyclically; the representations generated by the DFT circuit for any given cycle is based on a set of samples of a given size as, for example, 64 samples. In a given cycle, each DFT circuit receives a set of windowed samples from the associated buffer and windowing circuit and performs a discrete Fourier transform on this time domain data. The discrete Fourier transform yields representations of signal components at the carrier frequency and at other frequencies on the associated sensor coil. For example, DFT circuit 40x provides representations of signal components in the signals appearing on coil 30x, and so on. In the next cycle, the DFT circuit receives a new set of samples including N new samples together with the old samples used in the immediately preceding cycle with the earliest N old samples deleted, and generates a new representation is based on the new set of samples. The representation of the signal component at the carrier frequency includes a representation of its amplitude and phase. The phase representation is implicitly based on the timing of the samples used by the receiver. For example, a component at the carrier frequency crossing zero and increasing at the time of the first sample may be considered as having zero phase angle. The phase angle is determined by timing regime of the receiver.

The magnitude of the signal component at the carrier frequency in the signal from coil 30x, as recovered by DFT circuit 40x, is shown schematically in FIG. 2 on line C30x, whereas the magnitude of the signal component at the carrier frequency in the signal from coils 30y and 30z, recovered by DFT circuits 40y and 40z, is shown on the lines labeled C30y and C30z respectively. During transmission interval $T_X$, the magnitudes of the carrier-frequency component in each signal rises with the transmitted field $M_X$ to a stable value. However, these magnitudes differ from one another because the degree of magnetic coupling between receive coil 30x and transmit coil 10x differs from the corresponding degree of magnetic coupling between receive coil 30y or 30z and transmit coil 10x. Also, the phases of the carrier-frequency components in the receiver may differ from one another.

At the beginning of the next transmit interval $T_Y$ the carrier-frequency component in each signal takes some time to transition to a new stable value. During this transition, the carrier-frequency component of the signal from each receive coil 30 includes a part due to the decaying magnetic field $M_X$ from transmit coil 10x and a part due to the growing magnetic field from $M_Y$ from transmit coil 10y. Here again, the magnitude of the carrier frequency component from each receive coil 30 reaches a stable value after the transition period. There is a similar transition at the beginning of transmit interval $T_Z$, followed by stable magnitudes and then a further transition period at the end of $T_Z$.

The receiver control circuit 32 further includes a computation circuit 44 arranged to perform the computations and other operations discussed below.

Once buffers 37x, 37y, and 37z have been loaded with a full set of 512 samples, the DFT circuits performs a set of successive DFT cycles using successive sets of samples. Computation circuit 44 monitors the signal components computed by each of the DFT circuits 40x, 40y, and 40z in each cycle. For each cycle, the computation circuit determines the magnitude of the signal component at the carrier frequency found by each DFT circuit. The set of samples which yields the minimum magnitude for the carrier frequency component is selected as set $S_0$ marking the end of the quiet period. For example, if the DFT using a set of 64 samples beginning at the 401st sample and ending at the 465th sample yields the minimum magnitude of the carrier frequency component, the 465th sample time is considered as the last sample time in the quiet period. If two or more sets of samples yield the same values for the magnitude of the carrier frequency component, the last one of such sets is selected as set $S_0$. This process may be performed on all 512 possible sets of successive samples in the buffer, i.e., using only one new sample in each DFT cycle (N=1). To reduce processing load, however, the process may be conducted in a coarse manner, as for example, using 16 new samples in each cycle (N=16). After a sample set is selected in the coarse process, the process is repeated in a finer manner, such as with N=1, for only a small number of sample sets beginning from just before to just after the sample set selected in the coarse process. The sample set selected in the fine process is treated as set $S_0$ marking the end of the quiet period. The foregoing operations optionally can be performed using sample sets from only one of the three coils. In this manner, the computation circuit recognizes the marker denoting the end of quiet period $T_0$ and the beginning of transmit interval $T_X$.

In effect, the computation circuit treats the sample time of the last sample in a particular set $S_0$ as the end of $T_0$ and the beginning of $T_X$. As shown in FIG. 2, the last sample time of set $S_0$ may occur slightly before or after the exact beginning of transmit interval $T_X$. In practice, this delay time $T_D$ is typically a few sampling intervals at most, and can be neglected.

The computation circuit counts off a delay time $T_N$ corresponding to a predetermined number of sampling intervals after the identified end of the quiet period, i.e, after the end of set $S_0$. $T_N$ desirably is longer than the rise time and fall time of the drive circuits in the transmitter, and hence longer than the time required for the components at the carrier frequency to rise to stable magnitudes. In the embodiment shown, $T_N$ is equal to one-half of the transmission interval $T_X$, which in this case corresponds to 64 sampling intervals. The computation circuit then counts off an active sampling period beginning at time $T_{AX}$, beginning at time $Z_{AX}$ and having a duration which corresponds to a predetermined number of sampling intervals and, desirably, to an integral number of periods of the carrier frequency. In the embodiment depicted, $T_{AX}$ is one-half the duration of transmit interval $T_X$, i.e., 16 periods of the carrier frequency and 64 sampling intervals. The DFT circuits compute the magnitudes and phases of the carrier frequency components based on the stored samples from each sensor coil which were taken during the active sampling period $T_{AX}$.

The computation circuit takes these magnitudes and phases of the component at the carrier frequency as representing the magnitude and phase of the component in the signal from each sensor coil during the transmit interval $T_X$. The notation $C_{AB}$ is used in this disclosure to designate the carrier frequency component recovered from the signal appearing on each sensor coil. In this notation, A is an index denoting the particular sensor coil 30 which received the signal during a particular transmit interval, and B is an index denoting the particular transmit coil 10 which is active during that interval. For example, the carrier frequency component in the signal from X-direction sensor coil 30x during interval $T_X$ is designated $C_{XX}$, whereas the signal from sensor coil 30y during interval $T_Z$ is designated $C_{YZ}$. Thus, the magnitude and phase of the carrier-frequency component derived by DFT circuit 40x from the set of 64 samples of the signal from coil 30x taken during $T_{AX}$ represent component $C_{XX}$. Likewise, the magnitude and phase of the carrier-frequency component derived by DFT circuit 40y from the set of 64 samples of the signal on receive coil 30y taken during $T_{AX}$ component $C_{YX}$. Component $C_{ZX}$ is derived in the same way by DFT circuit 40z from the samples of the signal on receive coil 30z taken during $T_{AX}$.

As seen in FIG. 2, the active sampling period $T_{AX}$ may extend slightly beyond the end of transmit interval $T_X$. The duration of any such overlap is equal to $T_D$, the delay time from the end of quiet period $T_0$ the last sample time in set $S_0$ discussed above. Therefore, the sets of samples used to derive $C_{XX}$, $C_{YX}$ and $C_{ZX}$ will include a few samples taken during the transition at the beginning of transmit interval TY. However, these few samples do not cause serious errors in the phase and magnitude derived from the 64-sample sets.

Computation circuit 44 times out a dwell time $T_{XY}$ from the beginning of active sampling period $T_{AX}$. $T_{XY}$ is equal to an integral number of periods of the carrier frequency, i.e., $T_{XY}=n/f$ where n is an integer and f is the carrier frequency. In the illustrated embodiment, $T_{XY}$ is equal in duration to transmit intervals $T_X$, $T_Y$, $T_Z$, i.e., 32 periods of the carrier frequency, and thus n=32. The end $Z_{AY}$ of dwell time $T_{XY}$ falls within transmit interval $T_Y$, at a time when the magnetic field $M_Y$ from transmit coil 10y has reached a stable magnitude and the carrier-frequency components in the signals from the receive coils have also reached stable magnitudes.

The computation circuit times an active sampling period $T_{AY}$ beginning at the time $Z_{AY}$, i.e., at the end of dwell time $T_{XY}$. Here again, the active sampling period $T_{AY}$ desirably includes an integral number of periods of the carrier frequency, as, for example, 16 periods corresponding to 64 sampling intervals. The computation circuit and DFT circuits determine the magnitude and phase of carrier-frequency components $C_{YX}$, $C_{YY}$ and $C_{YZ}$ from the sets of samples taken by A/D converters 36x, 36y, and 36z, respectively during active sampling period $T_{AY}$.

The computation circuit 44 times a further dwell time $T_{YZ}$ from time $Z_{AY}$ (the end of $T_{XY}$ and beginning of active sampling period $T_{AY}$) to a time $T_{AZ}$. Dwell time $T_{YZ}$ is also an integral number of periods of the carrier frequency, and desirably is equal to $T_{XY}$, i.e., 32 periods. The computation circuit times an active sampling period $T_{AZ}$, which commences at time $Z_{AZ}$ during the stable-magnitude phase of transmit interval $T_Z$. $T_{AZ}$ desirably is equal in duration to $T_{AX}$ and $T_{AY}$, i.e., includes 64 sampling intervals. The computation circuit and DFT circuits determine the magnitude and phase of carrier-frequency components $C_{ZX}$, $C_{ZY}$ and $C_{ZZ}$ from the sets of samples taken by A/D converters 36x, 36y, and 36z, respectively during active sampling period $T_{AZ}$.

As pointed out above, the phase determined by DFT is implicitly referenced to the time of the first sample in the set of samples used in the DFT. However, the active sampling periods $T_{AX}$, $T_{AY}$, and $T_{AZ}$ are offset from one another by dwell times $T_{XY}$ and $T_{YZ}$ which are an integral number of periods of the carrier frequency. Therefore, the first sampling times in the various active sampling periods differ from one another by an integral number of periods of the carrier frequency. Stated another way, the phase references for all of the received carrier-frequency components $C_{XX}$ through $C_{ZZ}$ are equivalent to one another. As pointed out above, the transmitted magnetic fields sent during the transmit intervals are coherent with one another, and hence have the same zero phase. The mutually-equivalent phase references for the received components do not have any particular relationship to the zero phase of the transmitted magnetic fields. However, the offset between the zero phase of the transmitted magnetic field and the zero phase references used to determine the received components will be the same for all of the received components.

Figure 3:
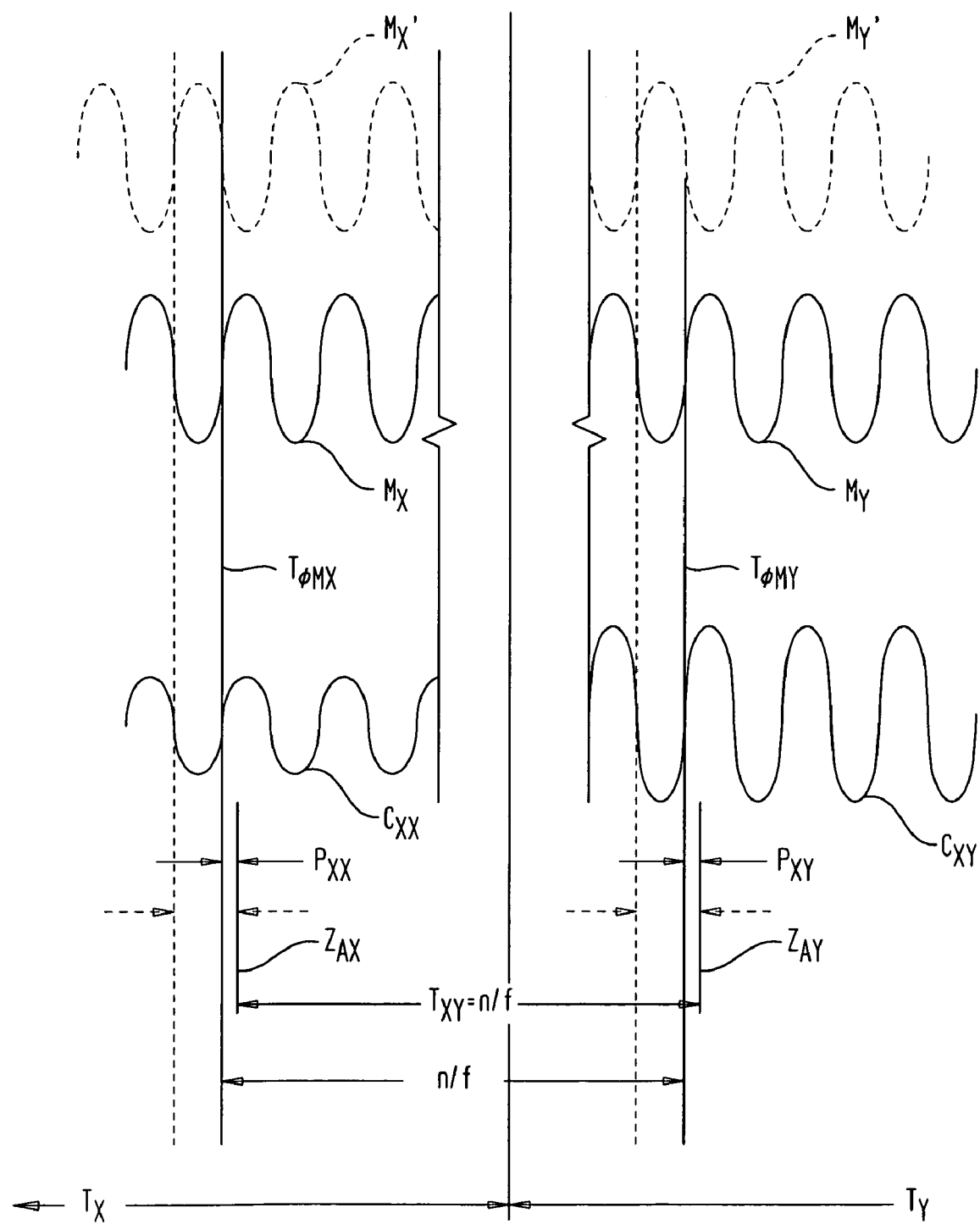
FIG. 3 is a further diagrammatic representation of certain signals used in the apparatus of FIG. 1.

This is schematically illustrated in FIG. 3. The transmit coils send alternating magnetic fields $M_X$ and My during transmit intervals $T_X$ and $T_Y$ respectively. The zero phase of each field is taken as the point where the field is at zero and increasing. Because these fields are coherent with one another, the zero phase $T_{0MY}$ of field $M_Y$ is separated from the zero phase $T_{0MX}$ of $M_X$ by an integral number of periods, i.e., n/f where n is an integer and f is the carrier frequency. These fields yield sensor coil signals having carrier frequency components $C_{XX}$ and $C_{YY}$. The starting time $Z_{AX}$ of the sampling period $T_{AX}$ used as the phase reference for $C_{XX}$ is at an arbitrary and unknown offset from the zero phase $T_{0MX}$. Therefore, component $C_{XX}$ has a non-zero measured phase $P_{XX}$. The starting time $Z_{AY}$ of the sampling period $T_{AY}$ (FIG. 2) used as the phase reference for measurement of $C_{XY}$ is separated from $Z_{AX}$ by an integral number of periods of the carrier frequency, i.e., n/f, and therefore the measured phase $P_{XY}$ of $C_{XY}$ is the same as the measured phase $P_{XX}$ of $C_{XX}$. The same relationship applies with respect to all of the components. Depending on the physical positioning of the coils, one or more of the measured component waveforms may be inverted, so that the measured phase of one or more components may differ from the measured phase of the other components by π radians (180°). Thus, the measured phase of each of the components will be either $P_{XX}$ or $P_{XX}+\pi$. The computation circuit subtracts $P_{XX}$ from the measured phase of each component to yield a corrected measured phase (0 or π) with a phase reference corresponding to the zero phase of the transmitted magnetic fields.

However, it is impossible to tell from examination of any one of the measured components whether the measured phase or the corrected measured phase is shifted by π radians from its correct value. For example, measured component $C_{XX}$ may be produced by transmitted magnetic field $M_X$ as discussed above, if the phase of $C_{XX}$ was not inverted due to the effects of coil positioning. However, the same measured component $C_{XX}$ would also occur if the transmitted field was $M'_X$ shown in broken lines in FIG. 2 and the phase of $C_{XX}$ was inverted due to the effect of coil positioning. This effect is referred to as "phase ambiguity" or "0 or π ambiguity." The same ambiguity applies to $C_{XY}$; this component may result either from transmission of $M_Y$ with no phase reversal due to positioning or from transmission of $M'_Y$ with phase reversal due to positioning. All of the other components suffer from the same ambiguity.

However, because all of the transmitted alternating fields are coherent with one another, there are only two possibilities for the entire system. If $M_X$ was transmitted, then $M_Y$ was also transmitted and the corresponding field $M_Z$ was sent during the other transmission interval $T_Z$. Conversely, if $M'_X$ was sent, then $M'_Y$ was also sent, and the corresponding field $M'_Z$ was sent as well during $T_Z$. Stated another way, either the measured phases (or corrected measured phases) of all of the components $C_{XX}$ through $C_{ZZ}$ are accurate, or all of them are incorrect by π radians.

Computation unit 44 forms a first matrix of the signal components as follows:

$$\begin{matrix} C_{XX} & C_{XY} & C_{XZ} \\ C_{YX} & C_{YY} & C_{YZ} \\ C_{ZX} & C_{ZY} & C_{ZZ} \end{matrix}$$

In this matrix, the rows correspond to the receive coils used to measure the signal components and the columns correspond to the transmit intervals and therefore correspond to the transmit coils used to form the signal components. The signal components used in forming the first matrix may have the original measured phases or the corrected measured phases as discussed above.

The computation unit then calculates the determinant of the first matrix. If the determinant is positive, then all of the corrected measured phases of all of the components are correct. In this case, the computation unit proceeds to derive the position and orientation of the sensor coils 30 in the frame of reference of the transmitter coils 10 based on the components $C_{XX}$-$C_{ZZ}$ as discussed below. However, if the determinant of the first matrix is negative, this indicates that all of the measured phases (or corrected measured phases) are incorrect by π radians. A negative determinant indicates a physically impossible spatial relationship between the transmit coils and the receive coils. If the determinant of the first matrix is negative, then the computation unit computes inverted components $C'_{XX}$ through $C'_{ZZ}$ by shifting the or corrected measured phase of each of the original components by π radians, i.e., adding π radians to the corrected measured phase of each component. Computation unit 44 then proceeds to calculate the position and orientation of the sensor coils 30 in the frame of reference of the transmit coils 10 based on the inverted components $C'_{XX}$-$C'_{ZZ}$ as discussed below. As a part of this calculation, the computation unit may form a second matrix identical to the first matrix discussed above, but incorporating the inverted components $C'_{XX}$-$C'_{ZZ}$ in place of the corresponding original, measured components $C_{XX}$-$C_{ZZ}$.

The algorithm used to derive position and orientation from the matrix of components is conventional, and is described in the aforementioned U.S. Pat. No. 4,737,794. Briefly, the algorithm solves the matrix equation:

$$S = \frac{k}{r^3} A^T P H P^T M$$

where:
S is a 3×3 signal matrix, which is the first matrix described above or the second matrix in the case where the determinant of the first matrix is negative;
k is a constant incorporating system and calibration constants;
r is the range of the sensor relative to the source;
A is an attitude matrix, i.e., a 3×3 orthogonal matrix representative of the orientation of the sensor;
P is a position matrix of 3 mutually orthogonal unit vectors, one of the unit vectors pointing toward the sensor from the source;
H is a field coupling matrix;
M is a source soil magnetic moment matrix; and
the superscript "T" following a letter designating a matrix indicates the transpose of the matrix.

In this equation, there are two unknowns: r and A. All of the other components are known by design or measured during a calibration process. Since the attitude matrix A is orthogonal, the operation $S^T S$ (where T indicates the transpose) removes the orientation information, because multiplying an orthogonal matrix by its transpose yields a unity matrix. This allows the resulting equation to be solved for the range r. Then, the range r can be put back into the equation and used to solve the orientation matrix A.

The receiver optionally is provided with an appropriate output device 46 for delivering the computed position and orientation. For example, the output device may be a radio transmitter for sending the position and orientation; a screen or other human-readable output device for indicating the position and orientation to a human user, or a link to some other electronic system for delivering the position and orientation in a format readable by such other system.

The system and method of operation discussed above with reference to FIGS. 1-3 provide an extremely simple system which can derive position and orientation. The system solves the problem of phase ambiguity simply, without the need for transmission of additional phase reference signals or other complicating elements.

Numerous variations and combinations of the features described above can be used. For example, the carrier frequency, transmission intervals and sampling intervals can be varied. In one such variation, the transmit intervals $T_X$, $T_Y$ and $T_Z$ are slightly longer than those discussed above and the intervals $T_{XY}$ and $T_{YZ}$ are correspondingly longer. This assures that each active sampling period $T_{AX}$, $T_{AY}$ and $T_{AZ}$ will fall entirely within the stable portion of a transmit interval. In still further variants, the transmit intervals may be of unequal lengths, and may be longer or shorter than the quiet period $T_0$. In the embodiment discussed above, the marker used by the receiver to coordinate its operations with the time-multiplexed sequence of magnetic fields includes the quiet period incorporated in the sequence of magnetic fields itself, and the structures which generate the marker include the same elements which generate the transmitted fields. Other methods of sending a marker from the transmitter to the receiver can be used as well. For example, the transmitter can include an audio, optical or radio frequency marker transmitting circuit separate from the circuits which generate the alternating magnetic fields. Desirably, any such separate transmitter operates at a frequency different from the carrier frequency. The marker transmitting circuit is synchronized with the circuits which send the alternating magnetic fields, so that the marker is sent in synchronism with some predetermined point in the sequence of transmitted magnetic fields. In these arrangements, the receiver desirably includes a marker receiver adapted to receive the separate marker signal as, for example, an optical, audio or radio frequency receiver.

Also, the multiplexing arrangement discussed above with reference to FIG. 1 is not essential; other circuits can be used to actuate the transmit coils 10 to send alternating magnetic fields coherent with one another during the various transmit intervals. For example, each drive circuit may be connected to a digital-to-analog (D/A) converter. Separate sequences of digital values may be read out from a memory and supplied to the D/A converters. The various sequences may be coordinated with one another so that the D/A converters will yield coherent signals during different transmit intervals.

A system according to a further embodiment of the invention uses a set of transmit coils 10 and received coils 30 and other components as discussed above with reference to FIG. 1. Here again, the transmit coils are actuated with a carrier-frequency signal during a sequence of transmit intervals $T_X$, $T_Y$, $T_Z$, so that only one transmit coil is active during each transmit interval. Here again, the sequence includes a quiet period $T_0$. In this embodiment as well, the transmit coils send alternating magnetic fields in the various transmit intervals, all of which are coherent with one another. In this arrangement, however, the alternating magnetic field at the carrier frequency is amplitude-modulated with a known waveform which increases progressively from zero magnitude at the beginning of each transmit interval and decreases progressively to zero magnitude at the end of each transmit interval. For example, the digital signal from carrier frequency generator 16 may be amplitude-modulated with a sinusoidal signal having a frequency $1/2T_I$ where $T_I$ is the duration of an individual transmit interval. The amplitude modulation is synchronized with the operation of the multiplexer. Thus, the amplitude of the carrier-frequency signal applied to each drive circuit increases and decreases gradually at the beginning and end of each transmit interval, and the magnitude of the magnetic field likewise increases and decreases gradually in a known, predictable manner. The receiver can detect the end of the quiet period $T_0$ in the same manner as discussed above. In each transmit interval, the receiver can use an active sampling period substantially equal to the entire transmit interval. Here again, the starting times of the active sampling periods desirably differ from one another by a dwell time which is an integral multiple of the period of the carrier frequency. The samples taken during each active sampling period may be pre-processed to reverse the effects of the amplitude modulation, i.e., by multiplying the time sequence of samples by a cosine signal having the same frequency as the sinusoidal amplitude modulation. In other respects, this system operates in the same manner as the systems discussed above.

In the systems discussed above, the alternating magnetic fields are coherent with one another. In a further embodiment, the alternating magnetic fields sent during the various transmit intervals have the same carrier frequency and have a known phase relationship, but are not coherent with one another. That is, the time from a particular phase of the waveform emitted during a first transmit interval to the corresponding phase of the waveform emitted during a second transmit interval is equal to an integral number of periods of the carrier frequency plus a known phase difference. The computation unit in the receiver can be arranged to subtract the known phase difference from the measured phase of each carrier frequency component obtained from during the second transmit interval. There may be a further known phase difference between the waveform emitted in the first transmit interval and a waveform used in a third transmit interval, and this may be compensated for in the same way. The coherent alternating fields discussed above with reference to FIGS. 1-3 constitute is a special case a known phase relationship, i.e., the phase differences are zero.

Likewise, the phase reference times used to measure the phases of the various carrier frequency components may differ from one another by delay times which are not integral numbers of periods of the carrier frequency, i.e., not equal to n/f, provided that the delay times are known, and therefore the difference between each delay time and an integral number of periods is known. The difference has the same effect as the known phase difference discussed above and can be corrected in a similar way, by subtracting or adding the difference to the measured phase of the affected carrier frequency components.

In the embodiments discussed above, the carrier frequency components are recovered by sampling the signals from the various coils and processing the samples digitally. However, other processes such as analog processing may be employed.

Larger or smaller sets of transmitting and receiving coils can be used. For example, a two-dimensional locating system can use fewer coils. Also, the technique used to correct the marker-frequency and main-frequency components can be used in applications other than locating systems.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A magnetic locating system comprising:
   (a) a transmitter including:
   (i) a plurality of co-located orthogonal transmit coils;
   (ii) a transmitting circuit operable to actuate the coils in alternating sequence so that the coils will emit a time-multiplexed sequence of magnetic fields $M_B$ during successive intervals of the sequence, where the subscript B denotes one of the transmit coils, each magnetic field varying at a carrier frequency f, such magnetic fields having a known phase relationship with one another; and
   (b) a receiver including:
   (i) a plurality of orthogonal sensor coils, whereby, when the sensor coils are exposed to the sequence of magnetic fields from the transmit coils, each sensor coil will generate a sensor signal during each transmit interval of the time-multiplexed sequence used by the transmitter;
   (ii) a receiver circuit operative to derive a set of components $C_{AB}$ at frequency f from the sensor signals, wherein the subscript A denotes the particular receiving coil which received such components and the subscript B denotes the transmitter coil active during the transmit interval, each such component $C_{AB}$ having amplitude and phase, the phases of the components being referenced to phase reference times, the phase reference times used in successive transmit intervals being offset from one another by known amounts; and
   (iii) a computation circuit operative to form a matrix of the signal components $C_{AB}$ with each row having the same value of A and each column having the same value of B, compute the determinant of the matrix and:
   (1) if the determinant is positive, calculate the position and orientation of the sensor coils relative to the transmit coils based upon the signal components $C_{AB}$; and
   (2) if the determinant is negative, derive inverted signal components $C'_{AB}$ corresponding to the signal components $C_{AB}$ phase-shifted by $\pi$ radians, and calculate the position and orientation of the sensor coils relative to the transmit coils based upon the inverted signal components.

2. A system as claimed in claim 1 wherein the transmitter includes means for sending a marker denoting a point in the time-multiplexed sequence and the receiver includes means for receiving the marker, the receiver circuit being operable to determine the intervals of the time-multiplexed sequence based on the marker.

3. A system as claimed in claim 1 in which the transmitting circuit is operable to actuate the coils to send a marker denoting a point in the time-multiplexed sequence and the sampling circuit is operable to detect a representation of the marker in one or more of the sensor signal components and determine the intervals of the time-multiplexed sequence based on the marker.

4. A system as claimed in claim 3 wherein the marker includes a quiet period during which none of the transmit coils is actuated.

5. A system as claimed in claim 1 wherein the transmitting circuit operable to actuate the coils so that the alternating magnetic fields emitted by the coils during the transmit intervals are coherent with one another.

6. A system as claimed in claim 5 wherein the transmitting circuit includes:
   (c) a plurality of coil drive circuits, each one of the transmit coils being connected to an associated one of the coil drive circuits;
   (d) a signal generation circuit for generating a signal at carrier frequency f; and
   (e) a multiplexer operable to connect the signal generation circuit to the coil drive circuits in alternating sequence.

7. A system as claimed in claim 5 wherein the phase reference times used in successive transmit intervals are offset from one another by dwell times wherein each dwell time is equal to n/f, where n is an integer and f is the carrier frequency.

8. A system as claimed in claim 7 wherein n is equal for all of the dwell times.

9. A system as claimed in claim 8 wherein all of the transmit intervals are of equal duration.

10. A system as claimed in claim 1 wherein the receiver circuit includes an plurality of A/D converters, one of the A/D converters being connected to each of the sensor coils for capturing a set of samples of each sensor signal during an active sampling period associated with each of the transmit intervals.

11. A system as claimed in claim 10 wherein the receiver circuit includes a discrete Fourier transform circuit, and the receiver circuit is operable to derive each of the components $C_{AB}$ by actuating the discrete Fourier transform circuit to perform a discrete Fourier transform on each of the sets of samples captured by the A/D converters during each active sampling period.

12. A system as claimed in claim 11 wherein the receiver is operative to actuate at least one of the A/D converters and the discrete Fourier transform circuit in a sliding DFT mode to capture successive samples and form successive sets by adding N newly-acquired samples to a previous set of samples and deleting the earliest N samples from the previous set, and to perform a DFT on each of the successive sets, and wherein the receiver circuit is operable to detect the end of a quiet period in which none of the transmit coils is actuated with the carrier frequency by determining the set which gives the minimum magnitude of a component at the carrier frequency in the DFT results.

13. A system as claimed in claim 11 wherein the active sampling periods associated with successive transmit intervals start at times which are offset from one another by known dwell times.

14. A system as claimed in claim 13 wherein each of the dwell times is equal to n/f where n is an integer and f is the carrier frequency.

15. A system as claimed in claim 10 wherein each active sampling period commences after the beginning of the transmit interval associated with such active sampling period.

16. A method as claimed in claim 15 wherein the alternating magnetic fields emitted by the coils during the transmit intervals are coherent with one another.

17. A method as claimed in claim 16 wherein the step of actuating the transmit coils includes applying a single signal at the carrier frequency to drive circuits associated with the coils in alternating sequence.

18. A method as claimed in claim 16 wherein the phase reference times used in successive transmit intervals are offset from one another by dwell times wherein each dwell time is equal to n/f, where n is an integer and f is the carrier frequency.

19. A method of magnetic locating including the steps of:
(a) actuating a plurality of co-located orthogonal transmit coils in alternating sequence to emit a time-multiplexed sequence of magnetic fields $M_B$ during successive transmit intervals, where the subscript B denotes one of the transmit coils, each magnetic field varying at a carrier frequency f, such magnetic fields having a known phase relationship with one another;
(b) sensing the alternating magnetic fields using a plurality of orthogonal sensor coils so that each sensor coil generates a sensor signal during each transmit interval of the time-multiplexed sequence used by the transmitter;
(c) deriving a set of components $C_{AB}$ at frequency f from the sensor signals, wherein the subscript A denotes the particular receiving coil which received such components and the subscript B denotes the transmitter coil active during the transmit interval, each such component $C_{AB}$ having amplitude and phase, the phases of the components being referenced to phase reference times, the phase reference times used in successive transmit intervals being offset from one another by known amounts; and
(d) using a non-human computation circuit, forming a matrix of the components $C_{AB}$ with each row having the same value of A and each column having the same value of B, computing the determinant of the matrix and:
(i) if the determinant is positive, calculating the position and orientation of the sensor coils relative to the transmit coils based upon the signal components $C_{AB}$; and
(ii) if the determinant is negative, deriving inverted signal components $C'_{AB}$ corresponding to the signal components $C_{AB}$ phase-shifted by $\pi$ radians, and calculating the position and orientation of the sensor coils relative to the transmit coils based upon the inverted signal components.

20. A method as claimed in claim 19 further comprising the steps of sending a marker denoting a point in the time-multiplexed sequence, detecting the marker, and determining the transmit intervals of the time-multiplexed sequence at the receiver based on the marker.

21. A method as claimed in claim 20 wherein the marker includes a quiet period during which none of the transmit coils is actuated.

22. A method as claimed in claim 21 wherein the step of detecting the marker includes detecting the end of the quiet period by detecting a component of a sensor signal at the carrier frequency.

23. A method as claimed in claim 19 wherein step of deriving the components includes sampling each sensor signal during an active sampling period associated with each of the transmit intervals to form a set of samples for such active sampling period.

24. A method as claimed in claim 23 wherein the step of deriving the components includes performing a discrete Fourier transform on each of the sets of samples for each active sampling period.

25. A method as claimed in claim 24 wherein the active sampling periods associated with successive transmit intervals start at times which are offset from one another by known dwell times.

26. A method as claimed in claim 25 wherein each of the dwell times is equal to n/f where n is an integer and f is the carrier frequency.

27. A method as claimed in claim 23 wherein each active sampling period commences after the beginning of the transmit interval associated with such active sampling period and wherein, during each transmit interval, the magnitude of the alternating magnetic field sent by a transmit coil stabilizes from the beginning of the transmit interval to the beginning of the active sampling period associated with that transmit interval.

\* \* \* \* \*

UNITED STATES PATENT AND TRADEMARK OFFICE
CERTIFICATE OF CORRECTION

PATENT NO. : 8,121,812 B2
APPLICATION NO. : 12/283296
DATED : February 21, 2012
INVENTOR(S) : Robert F. Higgins It is certified that error appears in the above-identified patent and that said Letters Patent is hereby corrected as shown below:

In the Specifications

Column 3, line 18, "coils is calculated" should read -- coils are calculated --.
Column 4, line 33, "out in these" should read -- out these --.
Column 4, line 61, "Preferably, the all" should read -- Preferably, all --.
Column 6, line 56, "cycle is based" should read -- cycle are based --.
Column 7, line 2, "representation is based" should read -- representation based --.
Column 7, line 42, "circuits performs" should read -- circuits perform --.
Column 9, lines 6-7, delete the paragraph break between "magnitudes" and "The".
Column 9, line 51, "My" should read -- $M_y$ --.
Column 13, line 22, "is a special case a" should read -- a special case of a --.
Column 14, line 47, "circuit operable" should read -- circuit is operable --.
Column 15, line 2, "includes an plurality" should read -- includes a plurality --.
Column 16, line 36, "wherein step" should read -- wherein the step --.

Signed and Sealed this
Ninth Day of July, 2013

Teresa Stanek Rea
*Acting Director of the United States Patent and Trademark Office*